(12) United States Patent
Pompee et al.

(10) Patent No.: US 9,980,723 B2
(45) Date of Patent: May 29, 2018

(54) DEVICE FOR ATTACHMENT OF PROSTHESIS

(75) Inventors: Christian Pompee, Saint Martin d'Uriage (FR); Patrick Carteron, Chalain le Comtal (FR); William Wiecek, Bonson (FR)

(73) Assignee: ASPIDE MEDICAL, La Talaudiere (FR)

( * ) Notice: Subject to any disclaimer, the term of this patent is extended or adjusted under 35 U.S.C. 154(b) by 1180 days.

(21) Appl. No.: 14/130,974

(22) PCT Filed: Jun. 26, 2012

(86) PCT No.: PCT/FR2012/051466
§ 371 (c)(1),
(2), (4) Date: Feb. 14, 2014

(87) PCT Pub. No.: WO2013/004947
PCT Pub. Date: Jan. 10, 2013

(65) Prior Publication Data
US 2014/0200587 A1 Jul. 17, 2014

(30) Foreign Application Priority Data

Jul. 7, 2011 (FR) ..................................... 11 56137
Jan. 17, 2012 (FR) ..................................... 12 50451

(51) Int. Cl.
*A61B 17/88* (2006.01)
*A61B 17/064* (2006.01)
(Continued)

(52) U.S. Cl.
CPC ........ *A61B 17/0642* (2013.01); *A61B 17/064* (2013.01); *A61B 17/068* (2013.01);
(Continued)

(58) Field of Classification Search
CPC ........ A61B 2017/0648; A61B 17/8875; A61B 17/864; A61B 17/865
See application file for complete search history.

(56) References Cited

U.S. PATENT DOCUMENTS

| 7,416,574 B2 * | 8/2008 | Udagawa ........... B01D 46/0001 219/400 |
| 2004/0034375 A1 | 2/2004 | Ruiz et al. |

(Continued)

FOREIGN PATENT DOCUMENTS

WO    WO 2007098512 A1    9/2007

OTHER PUBLICATIONS

International Search Report from parent PCT application PCT/FR2012/051466 dated Nov. 2, 2012, 5 pages.

(Continued)

*Primary Examiner* — Anu Ramana
(74) *Attorney, Agent, or Firm* — Tech Valley Patent, LLC; John Pietrangelo

(57) ABSTRACT

The device incorporates multiple implants for the attachment of prosthetic equipment, and is characterized by the fact that it incorporates multiple identical implants (1) positioned in alignment and connected to each other at their front (1*a*) and rear (1*b*), in a temporary manner, such that the said implants have a screw-form external configuration, and such that each implant has a longitudinal internal cavity (1*c*) of triangular cross-section extending fully from end to end, that constitutes the housing for a means of pre-positioning (3) configured to have a triangular imprint with a spiked-form end part (3*a*), such that the interconnection of the implants at the respective front and rear of two successive implants is a temporary connection, and such that the (Continued)

multiple implants constitute an assembled set intended to be inserted into a loader unit associated with the ancillary insertion device.

16 Claims, 4 Drawing Sheets

(51) Int. Cl.
    *A61B 17/068*     (2006.01)
    *A61B 17/10*     (2006.01)
    *A61B 17/00*     (2006.01)
    *A61B 17/04*     (2006.01)
    *A61B 90/00*     (2016.01)

(52) U.S. Cl.
    CPC ........ *A61B 17/105* (2013.01); *A61B 17/8872* (2013.01); *A61B 17/0467* (2013.01); *A61B 2017/00477* (2013.01); *A61B 2017/00526* (2013.01); *A61B 2017/0648* (2013.01); *A61B 2090/037* (2016.02)

(56) References Cited

U.S. PATENT DOCUMENTS

| | | |
|---|---|---|
| 2004/0230208 A1 | 11/2004 | Shayani |
| 2006/0282085 A1 | 12/2006 | Stone et al. |
| 2006/0282101 A1 | 12/2006 | DiCarlo et al. |
| 2007/0038220 A1 | 2/2007 | Shipp |
| 2011/0295282 A1 | 12/2011 | Glick et al. |
| 2012/0248171 A1 | 10/2012 | Bailly et al. |

OTHER PUBLICATIONS

Written Opinion from parent PCT application PCT/FR2012/051466 dated Nov. 2, 2012, 6 pages.

\* cited by examiner

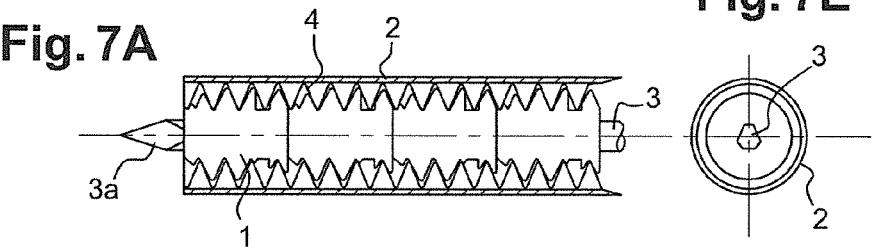
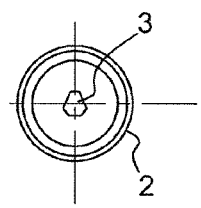
Fig. 7A
Fig. 7E
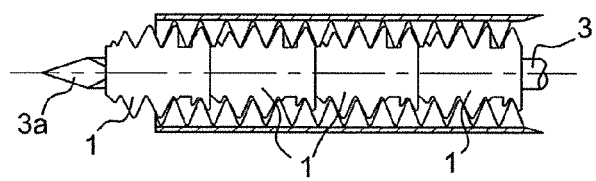
Fig. 7B
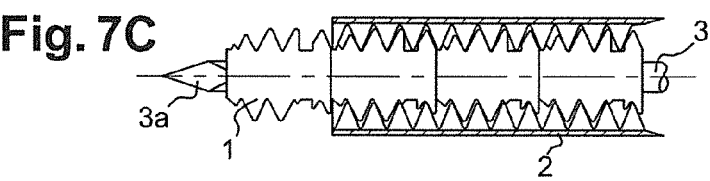
Fig. 7C
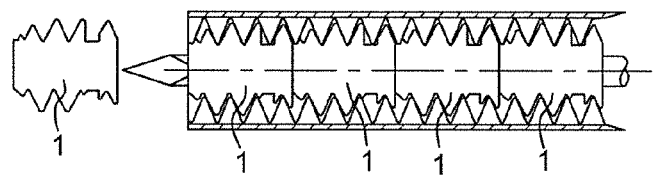
Fig. 7D

DEVICE FOR ATTACHMENT OF PROSTHESIS

CROSS-REFERENCE TO RELATED APPLICATIONS

This application is a § 371 filing of PCT application PCT/FR2012/051466 filed on Jun. 26, 2012, which claims priority from French application FR 1250451 filed on Jan. 17, 2012 and from French application FR 1156137 filed on Jul. 7, 2011. The disclosures of these applications are included by reference herein in their entirety.

BACKGROUND

Field of the Invention

The invention pertains to the technical field of implants used for attaching prosthetic equipment, such as prostheses (wall reinforcements) to soft tissues, and for enabling the connecting of soft tissues.

The invention more particularly concerns the implants or staples used for the attachment of prostheses in the treatment of abdominal hernia for the repairing of soft tissue and the reconstruction of abdominal walls.

Description of Related Art

The use and fitting of implants or staples is performed using guns with loaders filled with multiple implants or staples that are all separate from each other and that are disseminated by a command action on the trigger of the gun.

The problem is that the implants are guided in a more or less random manner from the loader to the tube or barrel of the gun intended to come into contact with the prosthesis via a trocar facilitating installation by laparoscopy. In practice, this results in a misalignment of the successive implants, which gives rise to jams and malfunctioning of the gun.

Different devices exist, such as those described in the patents US 2006/0 129 154, U.S. Pat. No. 7,758,612, US 2007/0 038 220, U.S. Pat. Nos. 5,431,669, 5,904,693, 5,743,880, 5,282,808, WO 93/24059, EP 1 317 213, EP 1 237 484, WO 2007/123978, FR 2 841 765, and WO 2007/123978.

The Applicant's approach was, therefore, to devise a new manner of disseminating the implants from a special gun, under conditions of better reliability, eliminating the risks of jamming and malfunctioning of the gun, which could be prejudicial during an operation in an operating room.

BRIEF SUMMARY OF ASPECTS OF THE INVENTION

The solution invented by the Applicant caters to the problem in a novel and unimagined manner.

According to a first characteristic of the invention, the device incorporates multiple identical implants positioned in alignment and connected to each other at their front and rear, in a temporary manner, such that the said implants have a screw-form external configuration, and such that each implant has a longitudinal internal cavity of triangular cross-section extending fully from end to end, that constitutes the housing for a pre-positioning device configured to have a triangular imprint with a spiked-form end part, such that the interconnection of the implants at the respective front and rear of two successive implants is a temporary connection, and such that the multiple implants constitute an assembled set intended to be inserted into a loader unit associated with the ancillary insertion device.

According to another characteristic, the set of interconnected implants is pinned onto the pre-positioning device configured with a triangular transversal cross-section, in view of loading them into the gun's loader tube.

According to another characteristic, each implant has a headless front part with a disc-form visible transversal front face; the implants are manufactured joined to each other in a detachable manner.

According to another characteristic, each implant has a front part having a semi-circular male assembly configuration in the form of a notch extending from the intermediate section forming the body of the implant, and a rear part with a semi-circular female assembly in the form of a notch extending from the intermediate section forming the body of the implant; the said parts of the assembly forming male/female notches fit together to constitute an assembly of successive implants allowing precise positioning within the loader unit by the said pre-positioning device.

According to another characteristic, the implant loader unit is tubular and accommodates a guide inside in the form of a sleeve having a regular screw profile, the said profile being designed to accommodate multiple implants constituting a one-piece set, and to enable their rotation and feeding into the unit by the rotation of the pre-positioning device, the said guide having a fixed position within the loader unit.

According to another characteristic, the deployment and positioning of implants in succession on the prosthesis to be attached is performed by presenting, by means of a pre-positioning device, the loader unit filled with the set of interconnected implants opposite the prosthesis to be attached, by presenting the pointed end of the said triangular-configuration pre-positioning device opposite the prosthesis and, by rotation, enabling the attachment of the immediately-positioned implant to the prosthesis, and then by withdrawing the said pre-positioning device via a rearward movement, which counter-thrusts on the next implant to the one has been fitted, creating sufficient thrust to detach and separate the fitted implant from the implant immediately adjacent, counteracting the retaining force generated by the attachment of the implant fitted onto the prosthesis, by the separation of their initially-connected walls.

These characteristics and others besides will be clearly understood by further reading of the description below.

BRIEF DESCRIPTION OF THE DRAWINGS

To clarify the purpose of the invention, non-limitative illustrations are provided, in which:

FIGS. 7A, 7B, 7C and 7D are large-scale views, in cross-section, illustrating the implant loader unit accommodating, in the optimized version, a regular-screw-pitch profiled guide able to receive and guide the entire implant unit, with the various views illustrating, as in FIGS. 3 to 6, the positioning and feeding of the implant unit, in view of separation of the one in the forward position;

FIG. 7E is a frontal view, according to FIG. 7A, of the implant loader unit including the guide;

DETAILED DESCRIPTION OF ASPECTS OF THE INVENTION

Figure 1:
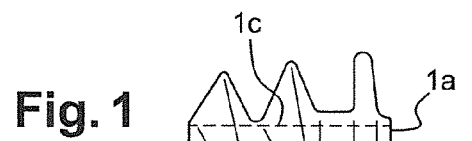
FIG. 1 is a view of just an implant according to the invention, implemented according to a first implementation variant.
Figure 2:
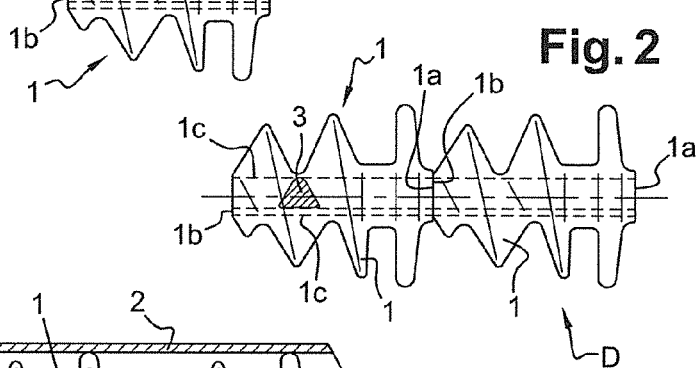
FIG. 2 is a view of a set of interconnected implants forming a homogeneous ensemble, in accordance with the configuration in FIG. 1.
Figure 3:
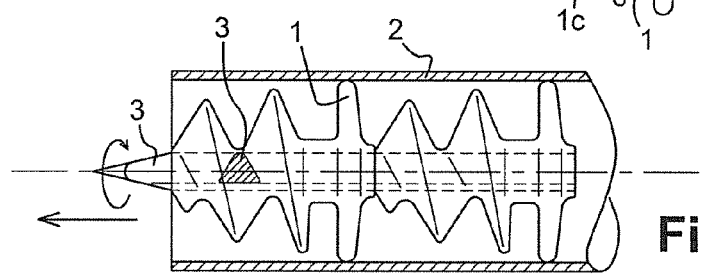
FIG. 3 is a schematic view illustrating the set of implants according to the invention, as per FIGS. 1 and 2, placed in a loader tube associated with a gun, with the set of implants being located in the loader tube.

In order to better clarify the purpose of the invention, it will now be described in a non-limitative manner, illustrated by the Figures.

The entire device according to the invention is referenced by (D). It includes a set of identical implants (i) positioned in axial alignment and interconnected to constitute, for example, a unit of 10 to 30 implants that can be mounted in a tubular implant loader unit associated with a fitting tool that can be an ancillary device of gun type, or a screwdriver. The said implants are connected at their front (1a) and rear (1b) in a temporary manner and then placed in a loader unit having a tubular configuration (2) intended to be positioned in a pre-positioning device. The loader unit is associated, by any appropriate manner, with the fitting ancillary.

According to an initial implementation illustrated in FIGS. 1 to 7, the said implants are connected at their rear and front during their manufacture. These said implants are detachable from each other, and they are formed into one whole during their manufacture with a temporary connection configuration. This connection can be a molecular bind, or can consist of lines or areas of weakening, depending on the production method. The implants can be produced by molding. The implants (1) have an exterior configuration in screw form. Their front part (1a) is headless with a disc-form visible transversal frontal face, and a rear part (1b) with a disc-form transversal face. Inside, each implant has, in its body (1d), a triangular-configuration longitudinal interior cavity (1c) that extends along the entire length of the implant, from its front face to its rear face. This cavity constitutes the housing for a pre-positioning device (3) configured as a section with a triangular imprint and a pointed protruding end (3a). Thus, the said positioning device (3) allows the pinning, in succession, of a set of interconnected implants. This pre-positioning device (3) is itself subjected to a rotation effect to allow the progressive feeding of the implants, the which is done by means of an appropriate control on the gun.

Now follows an explanation of the implant fitting process in this initial implementation variant.

Figure 4:
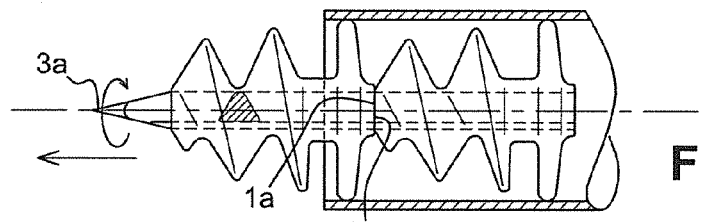
FIG. 4 is a view according to FIG. 3, showing the partial exit of an implant from the said loader.
Figure 5:
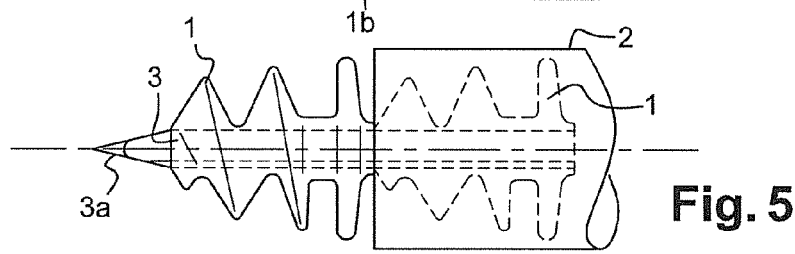
FIG. 5 is a view according to FIG. 4, illustrating the complete exit of an implant.
Figure 6:
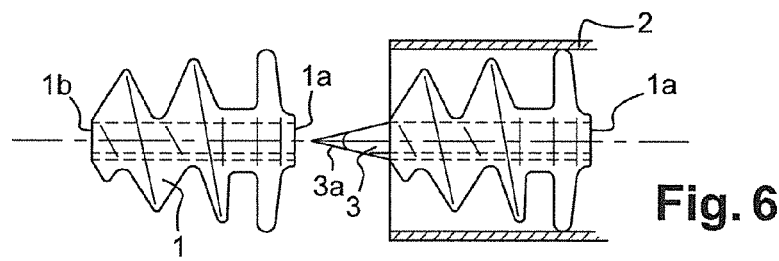
FIG. 6 is a view according to FIG. 5, showing the complete separation of an implant in relation to the entire implant unit, and the withdrawal of the pre-positioning device.
Figure 8:
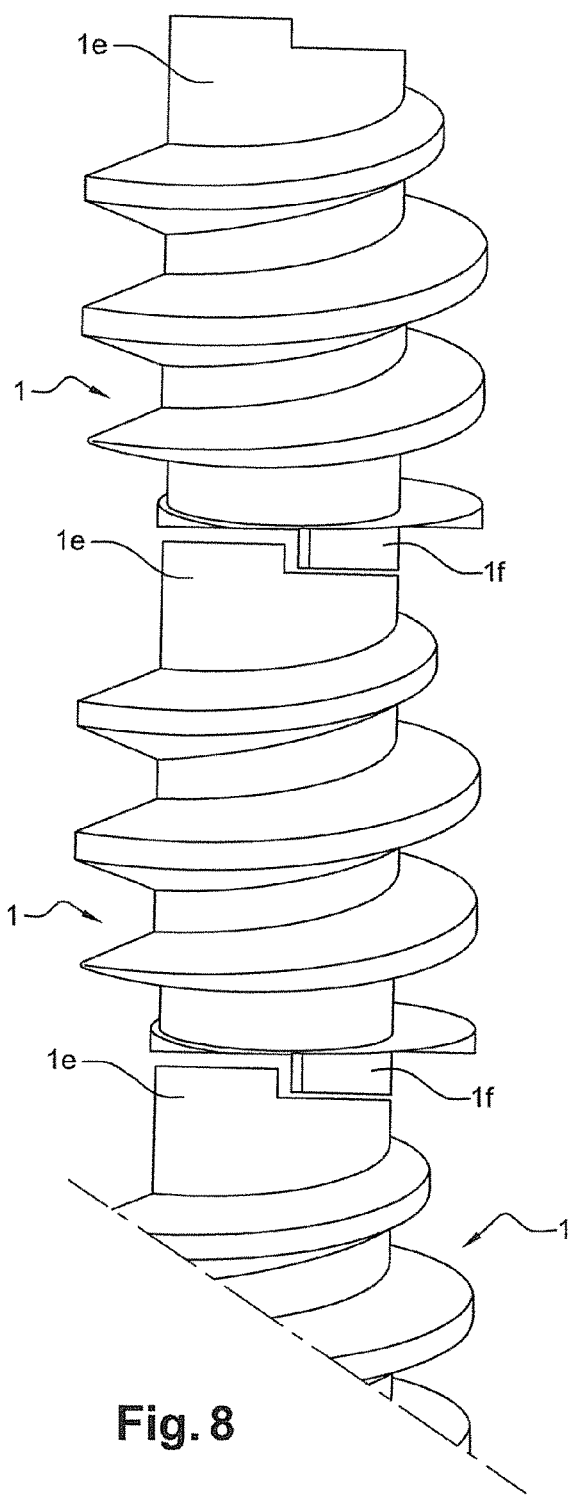
FIG. 8 is a view in perspective of a set of two implants intended to be assembled, according to a second implementation variant.

Previously, a set of interconnected implants is pinned by the pre-positioning device (3), having been inserted into the tube (2) associated with the gun's loader. The loader tube, with or without trocar, according to the application, is presented opposite the prosthesis to be attached, and the pointed end of the said device (3) is presented to the prosthesis. You then actuate the device (3) in rotation, to enable the implant to be screwed onto the prosthesis. As illustrated in FIGS. 4 and 5, the implant located at the front of the implant set is progressively exited from the loader unit (2), so as to be attached to the prosthesis. To ensure the separation of the fitted implant from the rest of the set, the device (3) is then withdrawn. This causes a thrust force that, contrary to the retaining force generated by the fixation of the implant attached to the prosthesis, causes the separation of the fitted implant from the rest of the implant set, by detachment from their initial connecting walls. The rotation of the device (3) and, therefore, the implants, and its advance or withdrawal, is done by any appropriate manner. The implants are made of bioresorbable materials, or of non-resorbable materials, but are compatible with their usage environment, such as well-known to an appropriately-knowledgeable professional.

Depending on the application conditions—for example, for laparoscopy and laparotomy techniques—the ancillary can be a one-time usage gun, or a multiple-usage re-sterilizable gun, or—where appropriate—a screwdriver.

In an optimized implementation illustrated in FIGS. 7A and 7E, the implants (1) loader unit (2), which notably provides external protection for the implants, accommodates a guide (4) inside, in the form of a sleeve of long length corresponding to the entire length or part of the length of the loader unit, and having a regular screw-pitch profile. This profile is designed to enable the accommodation of the implant set (1) constituting a one-piece whole while providing guidance for the said implants in rotation and in course of advance or withdrawal within the guide, in the manner of a nut, by actuation of the pre-positioning device (3). The regular-pitch profile of the guide is therefore matched to the screw profile of the implants. The guide has a fixed position within the loader unit.

The technical solution according to the invention enables one to apply what one might refer to as "pins" for a set of implants, or staples, that are perfectly guided by their respective connection in the tube of the loader associated with the gun. There is no risk that the implants can detach from each other while they are in position within the tube of the loader. Therefore, the gun can be used for continuous operations without risk of problems.

The number of implants pinned can vary according to needs and the configuration of the pistol, and as a function of the application.

The interconnection of the implants is advantageously molecular or by means of areas of weakening, but any other form of connection can be envisioned, the principal point being that it is temporary and that it can easily be destroyed after the attachment of an implant and withdrawal of the next unit.

In the variant illustrated in FIGS. 8 to 11, each implant (1) has the same interior configuration, with the triangular-configuration cavity (1c) extending along the entire length of each implant. However, each implant has a front part with a helical, semi-circular male assembly configuration (1e) forming a notch protruding from the intermediate part of the body (1d), and a rear part (1b) with a helical female assembly configuration (1f) forming a semi-circular notch protruding from the said intermediate part of the body (1d). Advantageously, the front parts (1a) and (1b) are of oblique transversal cross-section. By virtue of the helical configuration linked with the exterior screw-form configuration of the implant, the two notch-form male (1e) and female (1f)

assembly parts are complementary, and fit together by nesting so as constitute an assembly of two consecutive implants.

In this implementation, through the connection obtained, a rotational driving of the successive implants during the operation of the pre-positioning device is obtained (3).

For this purpose, and in accordance with an important arrangement, the guidance of the implants (1), in the two implementation variants in FIGS. 1 to 7 and 8 to 11, is obtained by the configuration of the accommodating loader unit (4), which is tubular but which has a groove (4a) on the interior in screw-pitch configuration, to guide the said implants and to enable their feeding.

Figure 11:
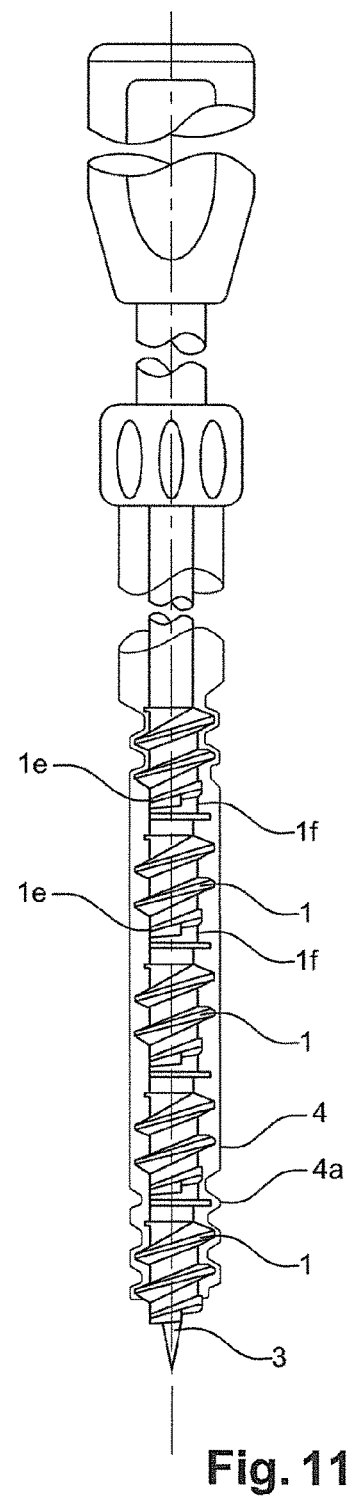
FIG. 11 is a view of a set of implants according to FIG. 8, inserted in a fitting tool composed of a screwdriver.
Figure 10:
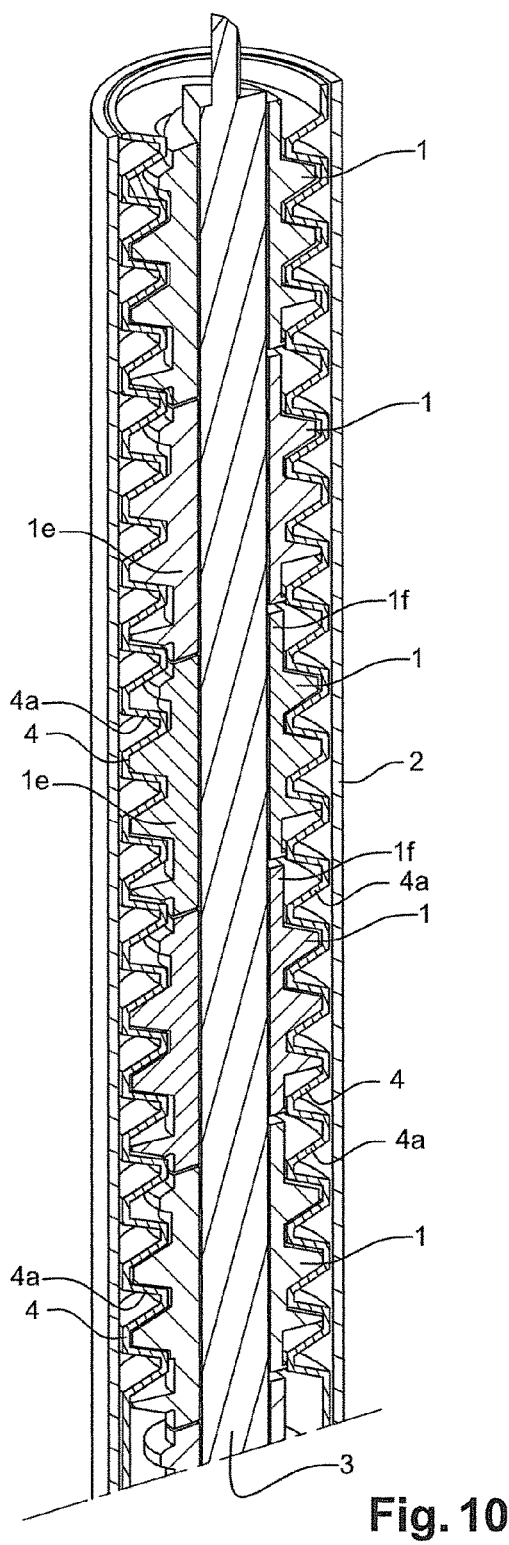
FIG. 10 is a schematic view illustrating the positioning of a set of implants according to FIG. 8, in a loader unit, which itself is inserted in the tubular conduit of a fitting tool.
Figure 9:
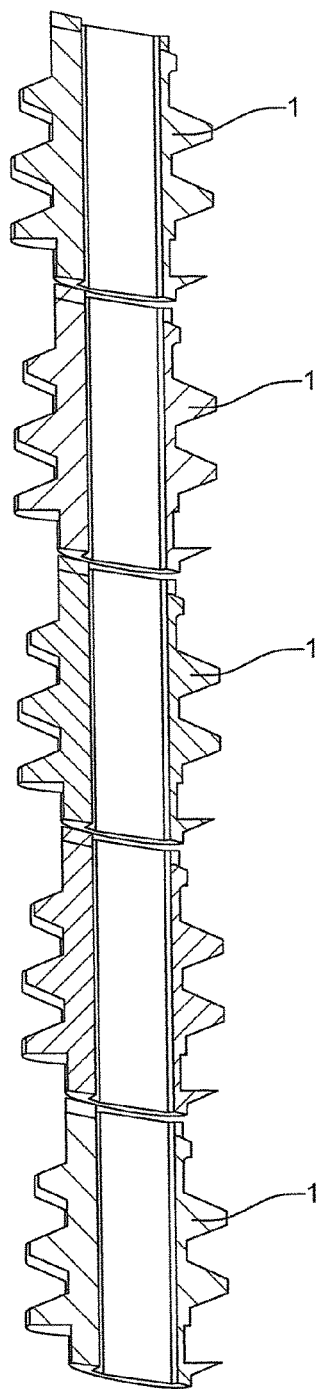
FIG. 9 is a perspective view of multiple implants implemented according to FIG. 8 and assembled with a partial longitudinal cross-section illustrating their respective positioning.

The said implants (1) can be disseminated by a tool of known art, namely a gun, but also by means of a screwdriver, such as illustrated in FIG. 11.

In the configuration in FIGS. 8 to 11, the implants (1) thus assembled by nesting are presented in a pin configuration on the receiving device (3).

The advantages of the invention are easily understood, and emphasis is placed on the new concept of implementation of the said implants.

The invention claimed is:

1. Device for the attachment of a prosthesis, the device comprising:
   multiple identical implants and a pre-positioning device;
   wherein the multiple identical implants include an engagement with each other at each implant's respective front and rear;
   wherein each of said multiple identical implants is externally threaded, and wherein each of said implants has a longitudinal internal cavity having a triangular-configuration cross-section and extending fully from front to rear of each of said multiple identical implants, and wherein said longitudinal cavity is adapted to engage the pre-positioning device;
   wherein said pre-positioning device comprises an elongated rod having an external surface shaped to engage the longitudinal cavity of each multiple identical implant; and wherein the pre-positioning device comprises a pointed end; and
   wherein the engagement of the multiple identical implants at each respective front and rear comprises a temporary engagement, and wherein said temporarily engaged multiple identical implants mounted to the pre-positioning device comprises an assembly of said multiple identical implants and pre-positioning device adapted to be inserted into a loader unit of an implant insertion device.

2. Device according to claim 1, wherein the triangular-configuration cross-section of the longitudinal cavity of each of the multiple identical implants comprises a triangular cross-section and wherein the elongated rod of the pre-positioning device comprises an elongated rod having a triangular cross-section.

3. Device according to claim 2, wherein the temporarily engaged multiple identical implants are produced by molding.

4. Device according to claim 2, wherein the device further comprises the loader unit, wherein the loader unit comprises an internally threaded sleeve adapted to accommodate the externally threaded multiple identical implants.

5. Device according to claim 1, wherein the front and rear of each of said multiple identical implants comprise planar faces; and wherein the engagement of said multiple implants comprises a joining of the planar faces.

6. Device according to claim 5, wherein the temporarily engaged multiple identical implants are produced by molding.

7. Device according to claim 5, wherein the device further comprises the loader unit, wherein the loader unit comprises an internally threaded sleeve adapted to accommodate the externally threaded multiple identical implants.

8. Device according to claim 5, wherein the device further comprises the loader unit, wherein the loader unit is tubular and comprises an internal thread adapted to guide the multiple identical implants.

9. Device according to claim 5, wherein the joining of the planar faces of the multiple identical implants comprises a connection that can easily be destroyed.

10. Device according to claim 5, wherein the joining of the planar faces of the multiple identical implants comprises a line or an area of weakening.

11. Device according to claim 1, wherein the temporarily engaged multiple identical implants are produced by molding.

12. Device according to claim 1, wherein the front of each of said multiple identical implants comprises a male projection extending from an intermediate section, and wherein the rear of each of said multiple identical implants comprises a female notch from the intermediate section; and wherein the engagement of the multiple identical implants comprises contact between the front male projection and the rear female notch.

13. Device according to claim 12, wherein the device further comprises the loader unit, wherein the loader unit is tubular and comprises an internal thread adapted to guide the multiple identical implants.

14. Device according to claim 1, wherein the device further comprises the loader unit, wherein the loader unit comprises an internally threaded sleeve adapted to accommodate the externally threaded multiple identical implants.

15. Device according to claim 14, wherein, upon rotation of the externally threaded multiple identical implants, engagement of the externally threaded multiple identical implants with the internally threaded sleeve of the loader unit feeds the externally threaded multiple identical implants along the loader unit.

16. Device according to claim 1, wherein the device further comprises the loader unit, wherein the loader unit is tubular and comprises an internal thread adapted to guide the multiple identical implants.

* * * * *